United States Patent [19]
Eichmann et al.

[11] Patent Number: 5,256,416
[45] Date of Patent: Oct. 26, 1993

[54] **EXTRACTS OF THE *ACANTHOSPERMUM HISPIDUM* PLANT**

[75] Inventors: Klaus Eichmann; Manuel Modolell, both of Freiburg, Fed. Rep. of Germany

[73] Assignee: Merck Patent GmbH Darmstadt 1, Fed. Rep. of Germany

[21] Appl. No.: 659,313

[22] PCT Filed: Jul. 27, 1990

[86] PCT No.: PCT/EP90/01231
§ 371 Date: Apr. 15, 1991
§ 102(e) Date: Apr. 15, 1991

[87] PCT Pub. No.: WO91/01741
PCT Pub. Date: Feb. 21, 1991

[30] Foreign Application Priority Data
Jul. 28, 1989 [DE] Fed. Rep. of Germany ....... 3925109

[51] Int. Cl.$^5$ .............................................. A61K 35/78
[52] U.S. Cl. .................... 424/195.1; 514/934
[58] Field of Search ...................... 424/195.1; 514/934

[56] References Cited
PUBLICATIONS
The Biology and Chemistry of the Compositae, Heywood et al., eds., Academic Press, 1977.
Bohlmann et al., Phytochemistry, 18, 625–630 (1979).
Jakupovic et al., Planta Medica, 154–155 (1986).
Nair et al., Phytochemistry, 15, 1776–1778 (1976).
Jain et al., Planta Med., 22(2), 136–139 (1972).
Jain et al., Planta Med., 20(2), 118–123 (1971).
Ali et al., J. Comp. Path., 88, 443–448; 533–544 (1978).
Munder et al., Augmenting Agents in Cancer Therapy, 441–458 (1981).

*Primary Examiner*—John W. Rollins
*Attorney, Agent, or Firm*—Birch, Stewart, Kolasch & Birch

[57] ABSTRACT

The invention relates to an aqueous extract of the *Acanthospermum hispidum* plant and its use as a medicament. The extract is effective as an immunomodulator, in the remedy of radiation sickness, in the prophylaxis and therapy of virus diseases and in the prophylaxis and therapy of retroviral diseases in mammals, and has an antitumor effect.

13 Claims, 9 Drawing Sheets

| CHANNEL | INT. (CPM) | PEAK (CPM) | T.HALF MAX. (RISE) | T.MAX | T.HALF MAX. (FALL) |
|---|---|---|---|---|---|
| 0 | | | | | |
| 1 | 11784 | 253 | 0 | 59.3 | > |
| 2 | 202951 | 5176 | 1.3 | 14 | 40 |
| 3 | 320952 | 8671 | 1.3 | 14.6 | 36.6 |
| 4 | 353411 | 9285 | 0.6 | 14.6 | 38 |
| 5 | 378097 | 10420 | 0.6 | 12 | 35.3 |
| 6 | 265981 | 7295 | 0.6 | 12 | 35.3 |

INTEGRATIONTIME FROM 0 TO 60 MIN
ALL CPM-VALUES X1000
FILE : AHMM917
DATE : 110987
USER : MM
COMMENT TO CHANNEL 1 : 200000 KMM 24 STD
COMMENT TO CHANNEL 2 : WIE 1 + 10 UL AH CH 2/9 KONZ
COMMENT TO CHANNEL 3 : WIE 2 + 10 UL AH 1/2
COMMENT TO CHANNEL 4 : WIE 2 + 10 UL AH 1/4
COMMENT TO CHANNEL 5 : WIE 2 + 10 UL AH 1/8
COMMENT TO CHANNEL 6 : WIE 2 + 10 UL AH 1/16

```
COMMENT TO CHANNEL 1 : 20 UL AH CH 2/7
COMMENT TO CHANNEL 2 : DTO
COMMENT TO CHANNEL 3 : 20 UL AH CH. 5/1
COMMENT TO CHANNEL 4 : DTO
COMMENT TO CHANNEL 5 : 20 UL AN CH. 2/8
COMMENT TO CHANNEL 6 : DTO.8.1X10E6. 53%GRAN, 47%LYMPHOS
```

EXTRACTS OF THE *ACANTHOSPERMUM HISPIDUM* PLANT

The invention relates to an extract of the *Acanthospermum hispidum* plant containing water-soluble components with a molecular weight >2,000.

The invention also relates to the use of the *Acanthospermum hispidum* extract as a medicament. Furthermore, the invention relates to the use of extracts of the *Acanthospermum hispidum* plant for the immunomodulation (influencing the immune state) of mammals, for the remedy of radiation sickness as well as for the prophylaxis and therapy of viral and retroviral diseases in mammals and for the therapy of tumors.

Finally, the invention relates to a method for producing an extract of parts of the *Acanthospermum hispidum* plant and effecting separation of the ingredients based on their molecular weight.

*Acanthospérmum hispidum* (compositae) is a plant originating from South America which has spread worldwide throughout the Tropics. In traditional medicine West Africans have used *Acanthospermum hispidum* (A.h.) for the production of tea (extracts) useful in the treatment of jaundice. Furthermore, A.h. is used in the treatment of Herpes labialis, the juice of the leaves being swabbed on the affected area.

The therapeutic effect of said extracts (as well as that of the leaf juice) in the treatment of Herpes labialis is the following: pain relief within one to three hours after application, reduction of the healing process to two to three days and extension of the relapse intervals. If this natural remedy is applied within the first few hours after the symptoms have begun to appear, it will usually completely suppress any lesion formation. The extract is also effective against Herpes genitalis.

A list of the ingredients of A.h. can be taken from the monograph "The Biology and Chemistry of the Compositae", V. H. Heywood, J. B. Harborne and B. L. Turner (eds.), Academic Press, London, New York, San Francisco, 1977. Melampolides, galactosides, acetylenes were isolated from A.h. by the F. Bohlmann group in Berlin, and their chemical structure was clarified. (Phytochemistry, 1979, Vol. 18, pages 625–630; Planta Medica, 1986, pages 154–155; Phytochemistry, 1976, Vol. 15, pages 1776–1778). The essential oils of said plant were studied to find out their microbial and antifungal effect (S.RR. Jain et al., Planta Medica, 1972, Vol. 22, page 136; and S. R. Jain and A. Kar, Planta Medica, 1971, Vol. 20, page 118). Toxicological studies on the use of A.h. as a fodder plant were conducted by B. Ali and I. Adam in goat and mice (J. Comp. Pathology, 1978, Vol. 88, pages 443–448 and pages 533–544).

However, *Acanthospermum hispidum* or an extract of said plant has not been used widely so far, as it has not been possible to administer it orally due to the toxicity of some of its ingredients.

Thus, the object underlying the invention is to provide a non-toxic but therapeutically active *Acanthospermum hispidum* preparation. This object is achieved by the surprising finding that the removal of low molecular components from the *Acanthospermum hispidum* extract causes the toxic effect of the extract to disappear.

Thus, one subject matter of the invention is the provision of an extract of the *Acanthospermum hispidum* plant containing the water-soluble components thereof with a molecular weight >2,000.

A further subject matter of the invention is the provision of the mentioned extract of the *Acanthospermum hispidum* plant for use as a medicament, especially as an immunomodulator, in the remedy of radiation sickness, in the prophylaxis and therapy of viral diseases or retroviral diseases in mammals and in the therapy of tumors.

It is preferred that the extracts of the invention be aqueous *Acanthospermum hispidum* extracts. However, there have also been used other extracting agents such as ethanol, chloroform, isopropanol, gasoline, and the like. The invention will be discussed hereinafter and exemplified by an aqueous extract. The term "aqueous extract" shall be understood to mean a substantially aqueous extract, i.e., it may contain small amounts of a non-aqueous solvent, e.g., not more than 10, preferably not more than 5% by volume, or a water-soluble compound, e.g., salts, sugar such as glucose, or acids such as ascorbic acid, as long as the substantially aqueous character of the extract is not affected.

To obtain the extract, fresh or dried *Acanthospermum hispidum* leaves are suspended in water, which may, if desired, contain any of the aforementioned additives, and homogenized at a temperature between 4° C. and 100° C., preferably at room temperature. The insoluble components are first separated by way of centrifugation and filtration. The supernatant and the filtrate, respectively, are freeze-dried so as to remove the volatile substances from the extract.

The product is then dissolved in destilled water, centrifuged to remove their insoluble components and subjected to a treatment for removing the components with a low molecular weight. It is preferred that centrifugation is effected at 100,000 g for an hour and dialysis is done against phosphate-buffered physiological salt solution (PBS). In another embodiment the low molecular components are separated out by way of ammonium sulfate precipitation. These steps ensure that components with a molecular weight <2,000 be removed from the extract. The below-described biological activities are contained in the macromolecular fraction.

The enzymatic treatment of the extract with trypsin, chymotrypsin, pronase, amyloglucosidase or DNAase does not change the activity thereof. Nor is its activity destroyed by heat (5 minutes, 100° C.), but what does destroy it is acidic hydrolysis or periodate oxidation. The portion of amino acids is very small, about 0.2%. The following sugars are contained in the extract: rhamnose, fucose, ribose, arabinose, xylose, mannose, glucose, and galactose.

The aqueous extract of the invention (hereinafter referred to as "A.h. extract") exhibits a number of biological activities:

1. Direct Antiviral and Antiretroviral Activity

It was shown in VSV (vesicular stomatitis virus), in MHV3 (mouse hepatitus virus 3), and in HIV (human immune deficiency virus).

VSV and HIV were incubated with A.h. extract and then titered with mouse fibroblast cell cultures (VSV) and MT4 cells (HIV), respectively, to measure the virus neutralizing effect of A.h. extract.

The results of these assays demonstrate that a lasting virus neutralization is achieved even with highly diluted A.h. extracts. The potential use of A.h. extract in the therapy of infected individuals was tested in mice which had been infected with MHV3 and administered either subcutaneously or orally different doses of A.h. extract.

Compared to control mice which had been likewise infected, but given no A.h. extract, a considerably increased survival rate was observed after administration of A.h. extract over a period of five days.

2. Positive Influence on the Immune State of Mammals

It was shown in human and mouse cell cultures by administration of A.h. extract.

In addition to the virus neutralizing effect a positive influence on the immune state was observed. Also, assays were carried out in different systems.

To see whether or not it was possible to induce the proliferation of B-lymphozytes, mouse spleen cells (CBF) were incubated with different A.h. amounts. The proliferation of the spleen cells was determined with $^3$H-thymidine or with alkaline phosphatase.

In the supernatants of the spleen cell cultures after 5 days the IgM concentration was measured, thus determining the stimulation of IgM synthesis in mouse spleen cell cultures. In further assays mouse bone marrow macrophages (KMM) were used to measure the stimulation of oxygen radical production and the induction of the proliferation of adult bone marrow macrophages. Analogous assays were made to stimulate oxygen radical production in human granulozytes and to induce the proliferation of peripheral human lymphocytes. In all these cases a clearly stimulating and inducing effect of A.h. extract on the cell cultures was observed.

It was possible to detect induction of interferon formation in mouse bone marrow macrophages. For that purpose bone marrow macrophages were incubated with different dilutions of A.h. extract for one hour and the cells, after washing, further cultivated without A.h. extract for an additional 24 hours. Interferon was detected in the supernatants of these cultures by neutralization of viruses. The system was stomatitis mouse virus.

3. Therapy of Radiation Sickness

It was done in mouse bone marrow macrophages which had been radiated with a soft X-ray source. The clearly increased survival rate of cells treated with A.h. extract as over non-treated cells was determined by reduction of a dye.

4. Tumor-Therapeutic Activity

It was shown in the effect on the mouse Meth A-fibrosarcoma.

Since the assays on the effect of A.h. extract revealed that both specific and unspecific defense mechanisms of the organism were stimulated, it surprisingly turned out that A.h. extracts possess a very strong antitumor effect which has been successfully tested in vivo in tumor-therapeutic models. The test model was a methyl cholanthrene induced transplantable mouse fibrosarcoma (Meth A-fibrosarcoma, induced by L. Old at the Sloan Kettering Institute for Cancer Research in N.Y., U.S.A.).

For that purpose a defined small amount of tumor cells is injected intracutaneously into the central abdomen of inbred mice which are genetically compatible with the fibrosarcoma. This tumor shows uniform, relatively rapid growth in all mice and results, without therapy, in the death of the animals within five weeks. It is easy to determine the size of the tumor, as it grows directly under the skin, thus being readily measureable from the outside.

In the assay CBF1 mice were injected intracutaneously with Meth A-fibrosarcoma cells into the shaved central abdomen. At days 3, 5 and 7 following implantation of the tumor, A.h. extracts were injected subcutaneously into the vicinity of the inginal lymph nodes. At days 7, 14, 21 and 28 after insertion of the tumors, their diameters were measured, and the tumor mass calculated. At the end of the assay, the number of cured animals was determined.

The therapy with A.h. extract first delays tumor growth, then shrinks the tumor mass and eventually results in tumor shedding in the majority of the animals. The extracts led to a regression rate of up to 100%, i.e., all the animals treated were cured. Long-term observation lasting several months revealed no relapse in the cured mice.

Of particular interest is the fact that the tumor shedding takes place at a time when therapy is already accomplished. This indicates that A.h. extract displays a long-lasting therapeutic effect.

Figure 1:
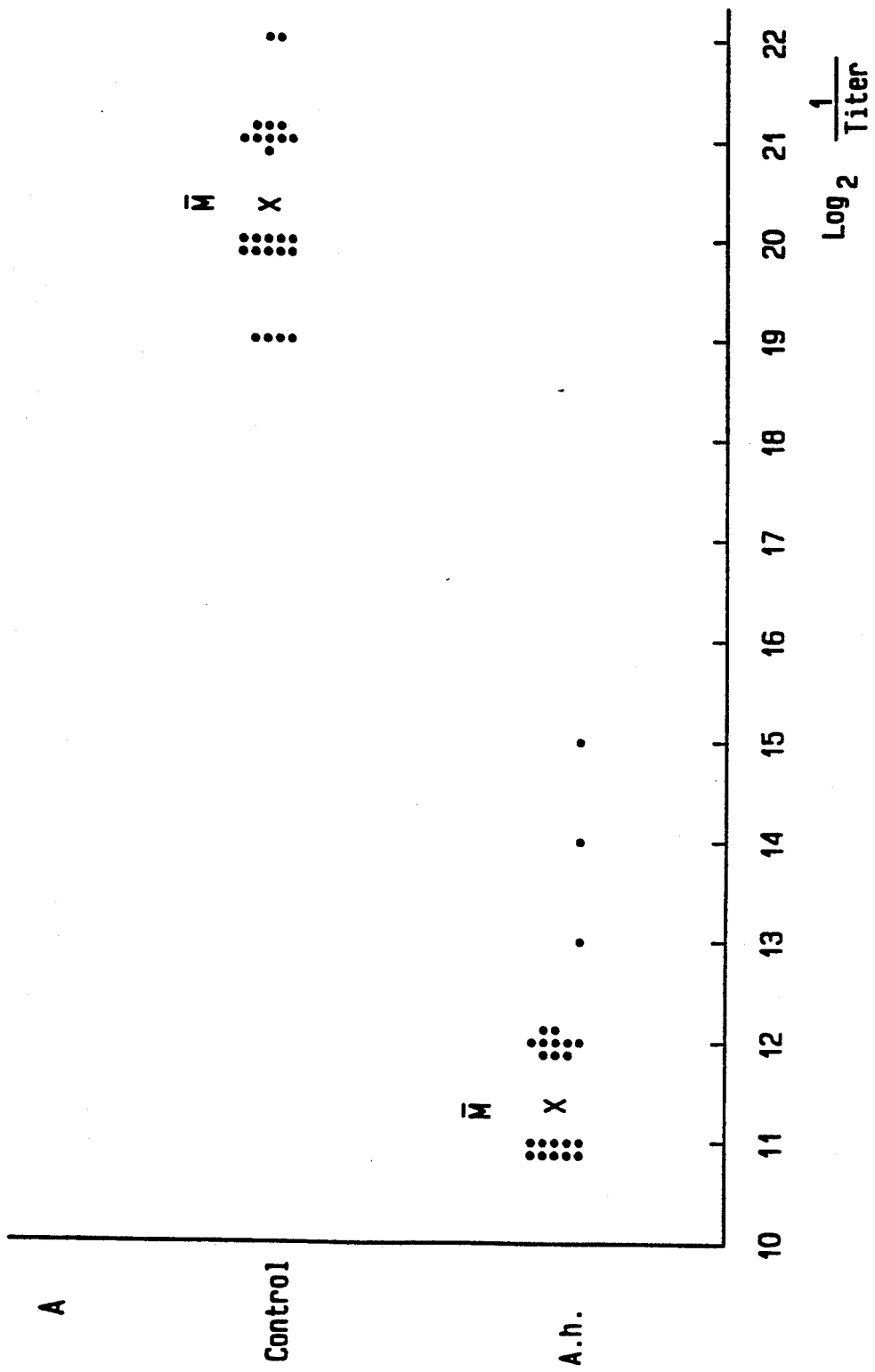
FIG. 1: the antiviral activity of A.h. extract against mouse VSV exemplified by L929 fibroblasts. Each dot shows the titer of the individual cultures with and without A.h. extract.
Figure 2:
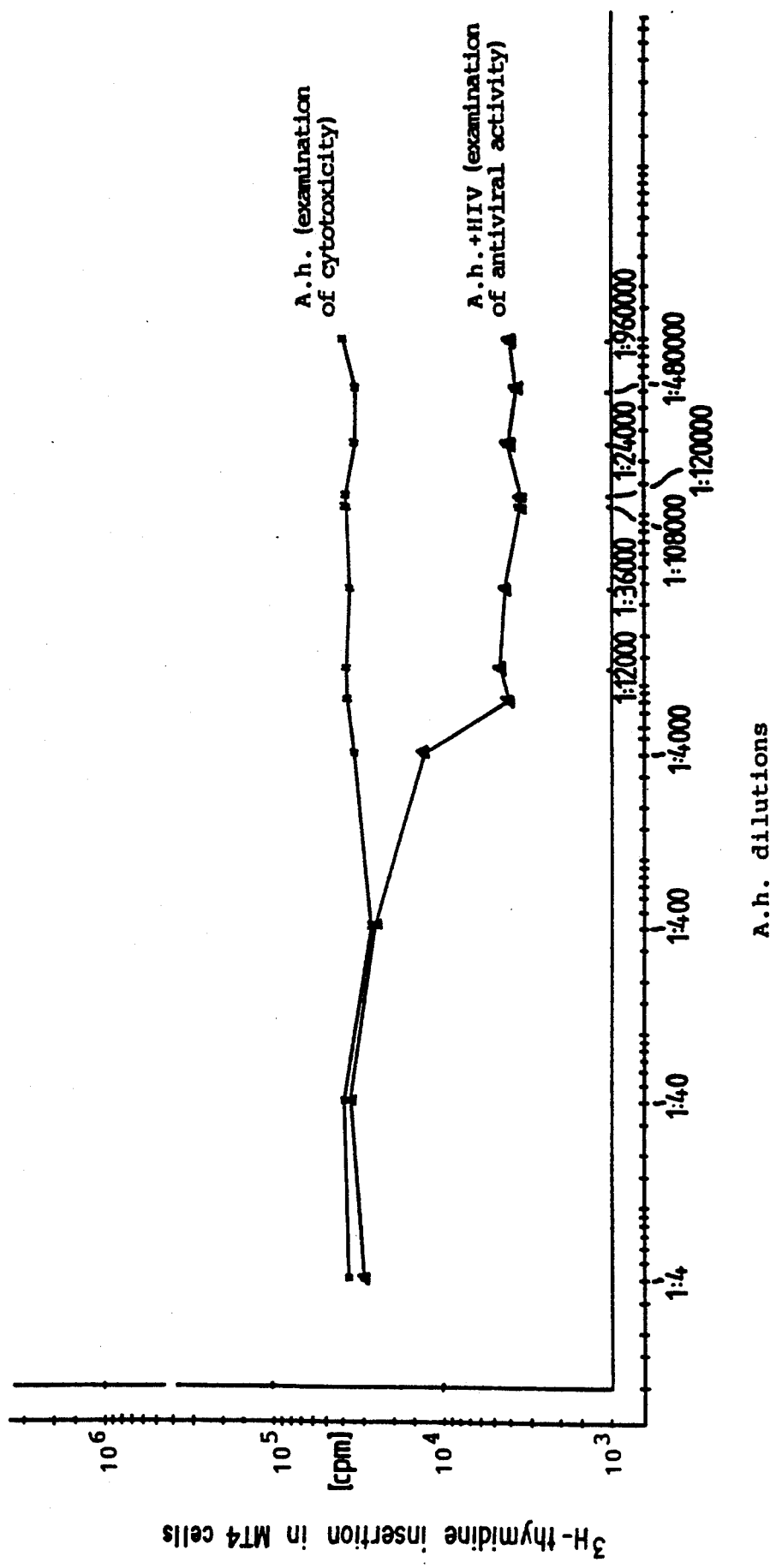
FIG. 2: the antiretroviral activity of A.h. extract against HIV, measured in MT4 cells. HI viruses are neutralized by A.h. extract until a dilution of 1:400 is obtained.
Figure 3:
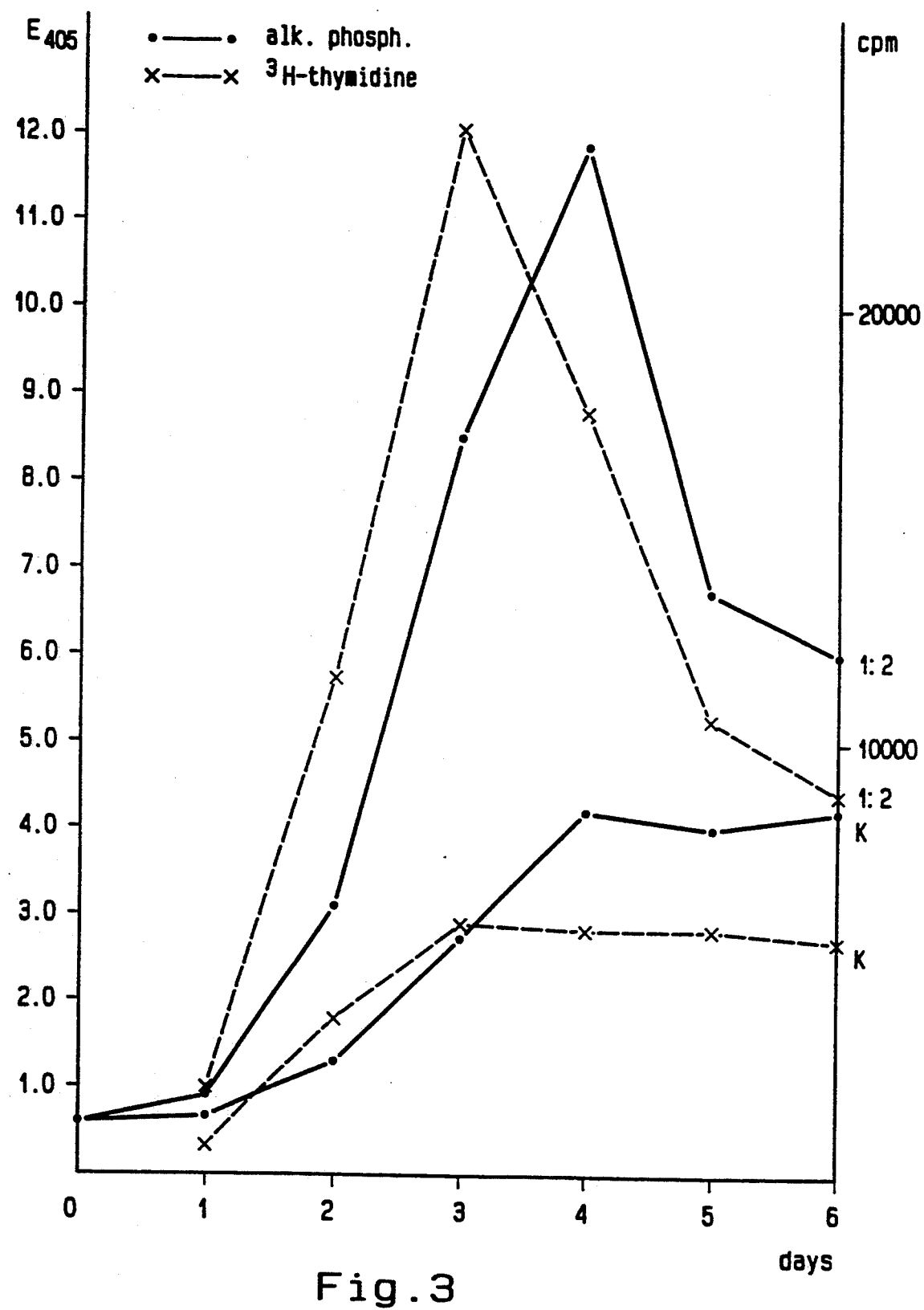
FIG. 3: the induction of the proliferation of B-lymphozytes of mouse CBF spleen cells. Proliferation is determined with H-thymidine or alkaline phosphatase.
Figure 4:
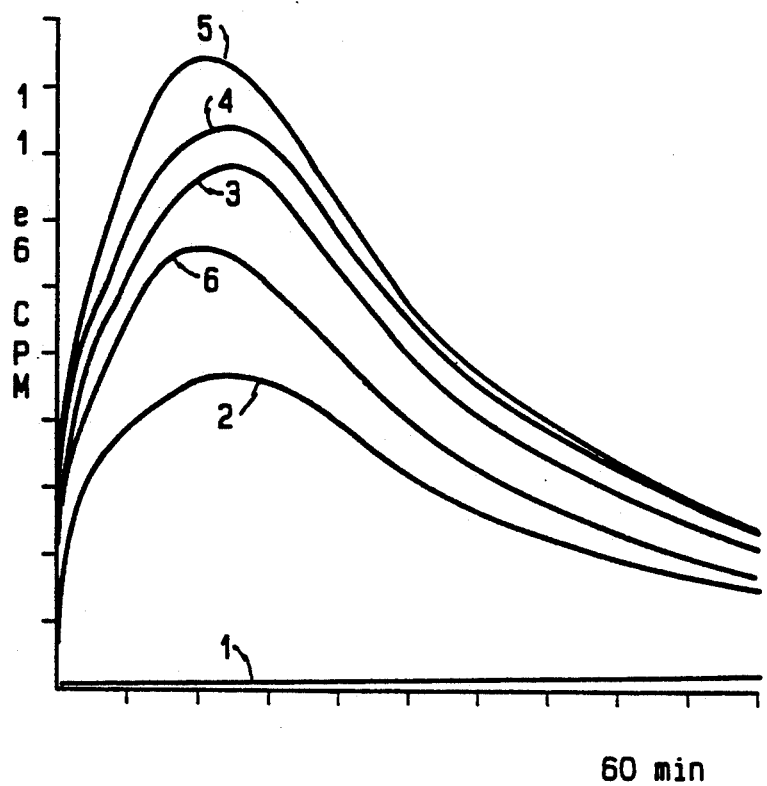
FIG. 4: the stimulation of mouse bone marrow macrophages. Determination is effected by conversion of short-lived oxygen radicals into light pulses. The oxygen radicals are received by lucigenin or luminol.
Figure 5:
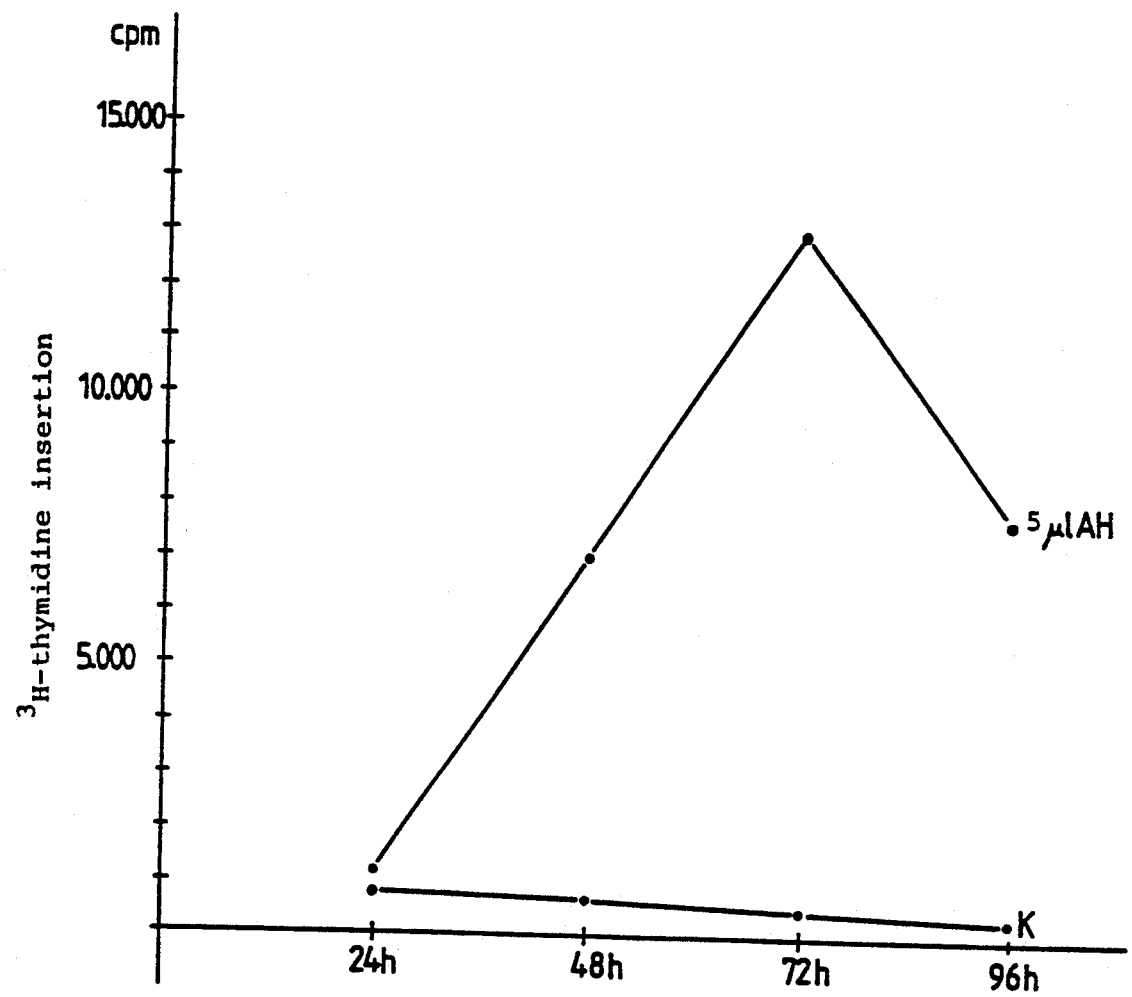
FIG. 5: the induction of the proliferation of adult mouse bone marrow macrophages, measured by $^3$H-thymidine insertion.
Figure 6:
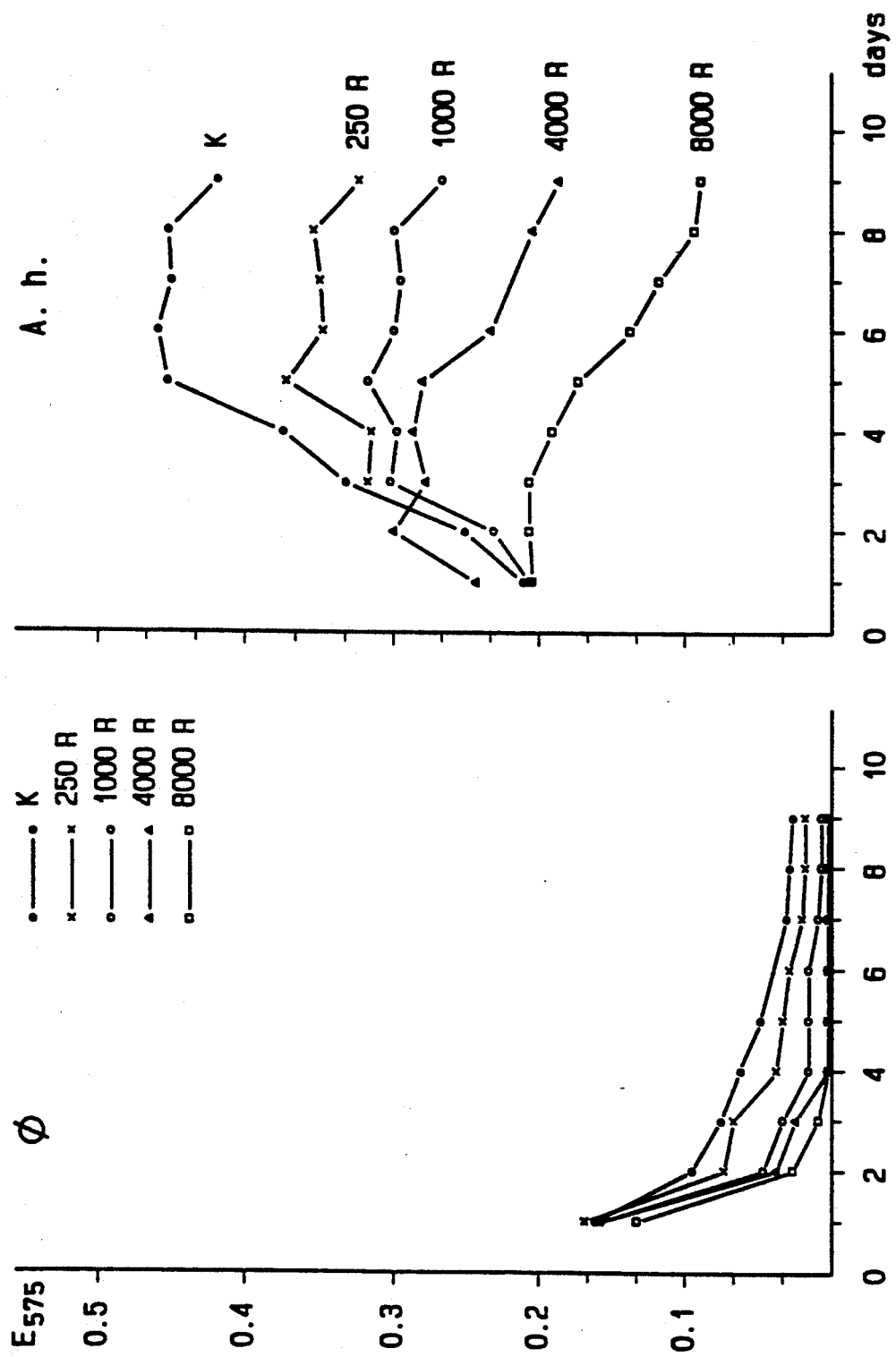
FIG. 6: the therapy of radiation sickness in mouse bone marrow macrophages. The viability test is done by photometric measurement (570 nm) of the reduction of MTT (3-(4,5-dimethyl-thiazole-2-yl)-3,5-diphenyltetrazolium bromide). Bone marrow macrophages are radiated at different doses using a soft X-ray source (60 KV, 25 mA). One hour after radiation, A.h. extract is added. After different cultivation times of the cultures with A.h. extract and controls without A.h. extract, the cells are mixed with 10 μl of MTT solution (5 mg/ml) and the extinction data determined.
Figure 7:
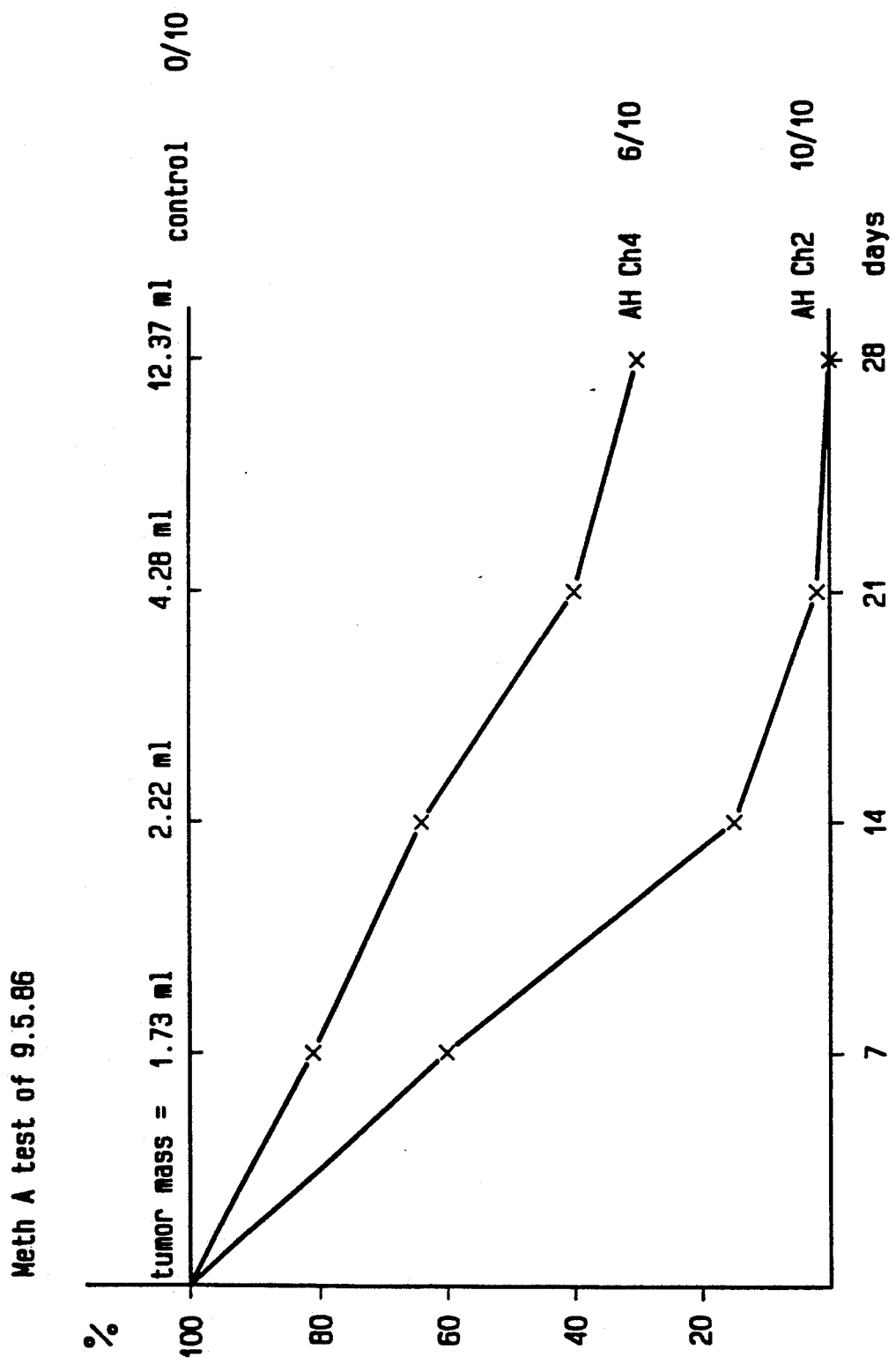
FIG. 7: the tumor-therapeutic activity of A.h. extract against mouse Meth A-fibrosarcoma. The mass of induced tumors is determined at days 7, 14, 21 and 28 after insertion of the tumor and injection of A.h. extract. The right-hand column indicates the number of cured animals and the total of assayed animals.
Figure 8:
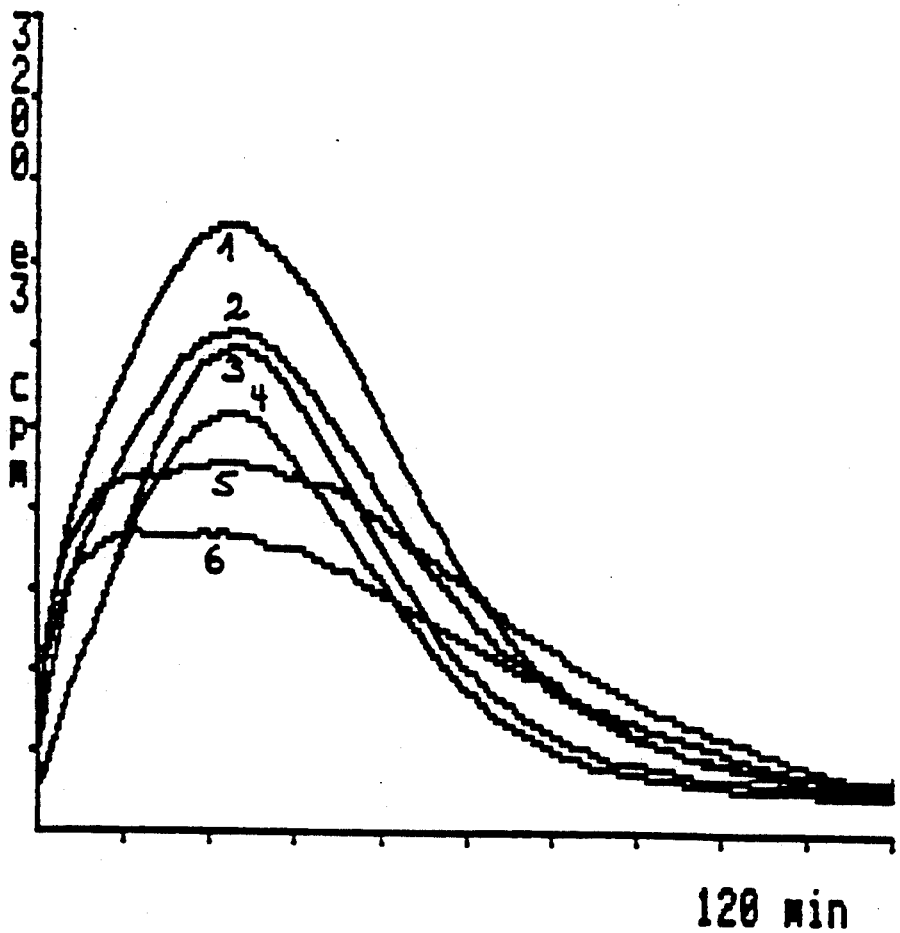
FIG. 8: the stimulation of oxygen radical production in human granulozytes. Measurement is analogous to the method indicated in FIG. 4.
Figure 9:
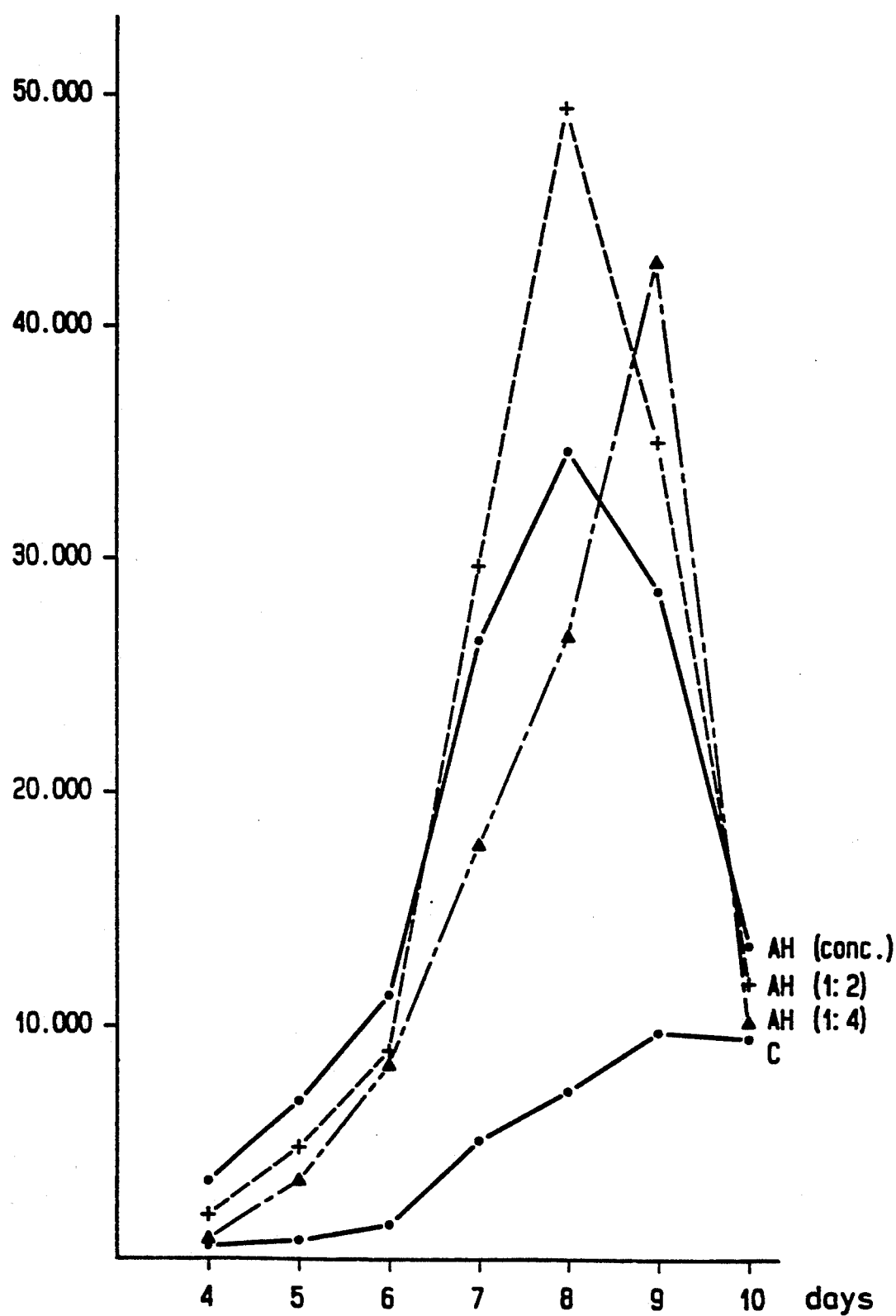
FIG. 9: the induction of the proliferation of peripheral human lymphozytes after administration of A.h. extract. The insertion of $^3$H-thymidine was measured.

The examples illustrate the invention.

EXAMPLE 1

*Production of Acanthospermum hispidum Extract from Fresh Leaves* a. One kg of freshly picked *Acanthospermum hispidum* leaves are washed twice with 5 liters of distilled water. The drained leaves are mixed with 1 liter of distilled water, poured into a homogenizer (e.g., Warring Blendor) and homogenized until the leaf parts are smaller than 1 mm². The temperature prevalent in the preparation during this process should not be in excess of 30° C. The leaf pulp is centrifuged at 6,000 g for 20 minutes. The supernatant is filtrated through a Whatman filter No. 1 and freeze-dried. The yield is about 30 g. This crude extract can be stored in a dry place at 4° C. until further use.

b. Six g of crude extract are mixed with 300 ml of distilled water, resulting in a turbid solution. The mixture is ultracentrifuged at 100,000 g for one hour at 4° C. Then the supernatant is dialyzed against 4×10 l of distilled water for 12 hours at 4° C. The dialyzed extract is either deep-frozen at −20° C. or freeze-dried. The yield is about 1.2 g.

c. For ammonium sulfate precipitation, 13.24 g of ammonium sulfate (final concentration 1M) are slowly added to 100 ml of dialyzed extract at 0° C. with constant stirring. By using a 25% ammonia solution, the pH is adjusted to 7.2. At 0° C., stirring is continued for an additional 30 minutes and so is precipitation. Then the mixture is centrifuged at 3,000 g for 10 minutes (4° C.). The supernatant (1M) is stored and the sediment resuspended in 10 ml of 1M ammonium sulfate solution for washing. The mixture is again centrifuged at 3,000 g for 10 minutes (4° C.) and the supernatant from washing discarded. Sediment 1M is dissolved in 30 ml of distilled water. To supernatant 1M there are slowly added 13.24 g of ammonium sulfate (final concentration 2M) at 0° C. with constant stirring. By using a 25% ammonia solution, the pH is adjusted to 7.2 and precipitation continued at 0° C. for 30 minutes. The mixture is centrifuged at 3,000 g for 10 minutes (4° C.). Supernatant 2M is stored. Sediment 2M is resuspended in 5 ml of 2M ammonium sulfate solution and again centrifuged at 3,000 g for 10 minutes (4° C.). The supernatant from washing is discarded. Sediment 2M is dissolved in 20 ml of distilled water. Sediment 1M, sediment 2M, and supernatant 2M are each dialyzed against 10 l of distilled water 4×12 hours at 0° C., and the dialysates are freeze-dried. The yield is: sediment 1M about 200 mg; sediment 2M about 50 mg; supernatant 2M about 95 mg.

EXAMPLE 2

*Production of Acanthospermum hispidum Extract from Dried Leaves*

200 g of air-dried leaves are crushed by means of a cutting mill. For swelling, the crushed leaves are mixed with 1 l of distilled water and stirred at 4° C. for 18 hours. The mixture is homogenized in a homogenizer (e.g., Warring Blendor) 3×60 seconds. The mixture is heated to 100° C. in a water bath for 10 minutes. Then it is centrifuged and freeze-dried as in Example 1. Further processing takes place as in Example 1, items b and c. The yield in crude extract is about 3.5 g, in dialyzed extract about 0.75 g, in sediment 1M about 5 mg, in sediment 2M about 55 mg, and in supernatant 2M about 85 mg.

EXAMPLE 3

Proliferation of Mouse Spleen Cells in the Presence of A.h. Extracts

Spleen cells are removed from inbred mice (e.g., CBF1, C3H, Balb/c) under sterile conditions. A cell suspension is prepared by means of a loose potter homogenizer. Following centrifugation (5 minutes, 700 g, 4° C.), the spleen cells are resuspended in tissue culture medium (DMEM). The medium contains the following additives: 10% fetal calf serum, 50$\mu$M 2-mercaptoethanol, 5 $\mu$g of streptomycin/ml and 100 I.E. penicillin/ml. The cells are adjusted to a concentration of 5,000,000/ml. 0.2 ml of cell suspension is poured into each hole of microtiter plates (of the flat bottom type). Then 10 $\mu$l of the various A.h. extract solutions (sterilized by filtration), respectively, are added. The microtiter plates comprising the cell cultures are incubated in a gassed incubator (37° C., 10% $CO_2$, 98% RH) for different periods of time according to the assay preparation. Parallel cultures are prepared so as to measure B-cell proliferation at different days. This is necessary because the cultures will be destroyed as a result of the harvest procedure after $^3$H-thymidine is added. To measure cell proliferation, the microtiter plates are centrifuged at 700 g for 10 minutes at room temperature. The cell sediments are mixed with 200 $\mu$l of new culture medium (plus the additives as above) and of 0.2 $\mu$Ci $^3$H-thymidine, respectively. After 6 hours of further incubation in a gassed incubator, the cells are harvested with a commercial harvester (e.g., Skatron cell harvester). Radioactivity in the cellular DNA is determined with a commercial $\beta$-scintillation counter.

Table I shows the results of an experiment of Example 3. The cells were incubated for four days prior to measuring proliferation. Proliferation is indicated in % with respect to the control. The figure in parentheses indicates the $^3$H-pulses per minute in the control. 10 $\mu$g of A.h. extract were added to each culture.

TABLE I

| Extracts: | control | dialyzed | 1 M | 2 M |
|---|---|---|---|---|
| % | 100 (5,730) | 370 | 528 | 237 |

EXAMPLE 4

Stimulation of IgM Synthesis in Spleen Cell Cultures by A.h. Extracts

Immunoglobulines of class M (IgM) are measured, as it is this antibody class which is primarily synthesized in vitro. The cultures are prepared on microtiter plates as in Example 3. After five days of incubation (37° C., 10% $CO_2$, 98% RH), centrifugation takes place at 700 g for five minutes at room temperature. 100 $\mu$l of each supernatant are removed and put on a new microtiter plate which has been pre-treated for the ELISA mouse IgM assay. The indicator reagent is an antimouse IgG (goat) antiserum which has been coupled with alkaline phosphatase. The antibody amounts are apparent from Table II and indicated in $\mu$g/ml.

TABLE II

| A.h. ($\mu$g) (dialyzed) | — | 5 | 2.5 | 1.25 | 0.625 |
|---|---|---|---|---|---|
| IgM ($\mu$g/ml) | 2.4 | 17.0 | 12.5 | 7.8 | 5.3 |

EXAMPLE 5

Proliferation of Mouse Macrophages by A.h. Extracts

The macrophages are grown in vitro according to the Metcalf method. For this purpose bone marrow cells from a mouse femur are isolated and cultivated in a culture medium (DMEM) containing 30% of fibroblast culture supernatant from cell line L929 and 5% of horse serum. These additives cause the parent cells to proliferate and differentiate exclusively in macrophages. After 10 days of incubation, these cultures only consist of pure macrophages which show no proliferation any more. By the addition of A.h. extracts, they surprisingly start anew to divide without dedifferentiating taking place. Said proliferation is measured as follows:

20,000 macrophages are mixed with 200 µl of culture medium (as in Example 3) and poured into each hole of microtiter plates. Thereto are added 10 µl of the various A.h. extracts, respectively. In a gassed incubator the mixture is incubated for four days and then centrifuged at room temperature (700 g/5 minutes). If desired, the supernatants are stored for interferon determination. 200 µl of culture medium and of 0.2 µCi $^3$H-thymidine, respectively, are pipetted onto the cells. Then incubation is continued in the gassed incubator for an additional 24 hours. The microtiter plates comprising the cultures are frozen at $-20°$ C. to remove the macrophages adhering to the culture flask and thawed, and the radioactivity of the cellular DNA is determined as in Example 3.

EXAMPLE 6

Determination of Interferon Induction by A.h. Extracts in the Mouse Bone Marrow Macrophage Culture 100,000 macrophages are mixed with 200 µl of culture medium (DMEM; as in Example 3) and poured into each hole of microtiter plates.

Using different A.h. dilutions, the mixture is incubated for one hour. The cells are washed once in culture medium and cultivated for an additional 24 hours in the absence of A.h. extract. Then the supernatants are removed by means of a pipette for interferon determination.

Interferon determination is based on the neutralization of the virus of the vesicular stomatitis of the mouse. Said virus is capable of infecting mouse fibroblasts (cell line L929) and destroying them by virus proliferation and secretion. Said cytopathological effect can be observed microscopically.

For that purpose 20,000 L929 cells are sown in 100 µl of culture medium on microtiter plates. 100 µl of the macrophage culture supernatants or, as controls, A.h. extracts (diluted in 100 µl of medium) are added. The microtiter plates are incubated in a gassed incubator for 24 hours (37° C., 10% $CO_2$, 98% RH). 10 µl (corresponding to 7,000 infectious units) of vesicular stomatitis virus (VSV) are added in each hole. Then incubation is continued in the gassed incubator for an additional 48 hours. Cell destruction (cytopathic effect) or possible inhibition by interferon in the culture is read microscopically.

Table III shows the results of such an experiment. The negative signs indicate cell destruction (cytopathic effect), the positive its inhibition by the presence of interferon.

TABLE III

| A.h. extract (µg/culture) | – | 20 | 10 | 5 | 2 | 1 | 0.5 |
|---|---|---|---|---|---|---|---|
| IF | – | + | + | + | + | + | – |

EXAMPLE 7

Stimulation of Oxygen Radical Production in Mouse Bone Marrow Macrophages

Macrophages from the bone marrow are grown in teflon bags according to the Metcalf method (see Example 5). Measurement is taken by conversion of the very short-lived oxygen radicals into light pulses. For this purpose substances such as lucigenin or luminol which serve as receptors for oxygen radicals are used. As a result of oxidation processes, photons are formed which are measured by commercial apparatuses (Biolumat manufactured by Berthold). The assay preparation is made as follows: 200,000 bone marrow macrophages are incubated in 0.2 ml of DMEM without phenol red and $NaHCO_3$ with 50 mM Hepes as a buffer at 37° C. for one hour. Measurement is taken after adding 0.2 ml of DMEM, 10 µl of lucigenin solution (11.6 µmole), and 10 µl of the corresponding A.h. dilution (1 mg/ml).

EXAMPLE 8

Therapy of Radiation Sickness in Mouse Bone Marrow Macrophages

Mouse bone marrow macrophages are radiated with a soft X-ray source (60 KV, 25 mA). The viability of the cells is determined by means of reduction of MTT (3-(4,5-dimethylthiazole-2-yl)-3,5-diphenyltetrazolium bromide). 100,000 KMM are incubated in each hole. The A.h. extract is added one hour after radiation. After different cultivation times, the cells are mixed with 10 µl of MTT solution (5 mg/ml), the plates are centrifuged after 4 hours of incubation at 37° C., the culture medium is removed and the tetrazolium blue crystals are dissolved in 100 µl of isopropanol - 0.04M HCl.

The color is read in a microtiter photometer at 570 nm.

EXAMPLE 9

Tumor-Therapeutic Activity on the Mouse Meth A-Fibrosarcoma

CBF1 mice are each injected intracutaneously with 50,000 Meth A-fibrosarcoma cells in the shaved central abdomen. At days 3, 5, and 7 following tumor implantation, 1 mg of A.h. extract is injected subcutaneously into the vicinity the inginal lymph nodes. At days 7, 14, 21, and 28 after insertion of the tumors, their diameters are determined. As tumors do not grow in a totally round shape, the smallest and largest diameter is measured using a slide gauge. The tumor mass is calculated according to the formula $$V = \frac{4}{6} \pi \cdot a \cdot b \cdot \left( \frac{a+b}{2} \right)$$

which corresponds to the volume of half an ellipsoid.

EXAMPLE 10

Induction of the Proliferation of Peripheral Human Blood Lymphozytes (PBL) by A.h. Extracts 20 ml of heparinised whole blood (5 I.E. heparin/ml) are diluted with 60 ml of physiological salt solution. 5 ml of Ficoll Isopaque solution (density 1.17) are poured into centrifuge tubes and covered with 5 ml of the diluted blood. Centrifugation takes place at 1,700 g for 30 minutes at 23° C. The cells which are found between the lower (Ficoll Isopaque) and the upper (diluted plasma) phase are removed by means of a pipette. The cells are then diluted with the 10-fold volume of physiological salt solution. The mixture is centrifuged at 700 g for 10 minutes at room temperature and the supernatant discarded. The cell sediment is resuspended twice in 10 ml of physiological salt solution and centrifuged as above. The cell sediment is mixed with DMEM+fetal calf serum+additives (see Example 3) and adjusted to a concentration of 500,000 cells/ml. Each hole of microtiter plates (of the flat bottom type) is filled with 0.2 ml of cell suspension (100,000 PBL each hole). In the holes there are added 10, 5, 2.5, 0 $\mu$g of the A.h. extract solutions. The microtiter plates comprising the cell cultures are incubated in a gassed incubator (37° C., 10% $CO_2$, 98% RH) for four days. The cultures are centrifuged at 700 g for 10 minutes at room temperature and the supernatants discarded. The cell sediments are mixed with 200 $\mu$l of culture medium +additives +0.2 $\mu$Ci $^3$H-thymidine, respectively. After 24 hours of further incubation in the gassed incubator, the cells are harvested, and the radioactivity in the cellular DNA is determined as indicated in Example 3.

EXAMPLE 11

Direct Antiviral Activity Against Vesicular Stomatitis Virus (VSV)

0.5 ml of VSV with a titer of 2×10 infectious particles/ml are incubated with 2.5 $\mu$g of A.h. extract in Hepes buffered DMEM at 23° C. for one hour. This preparation and the corresponding control without A.h. extract are diluted with DMEM in logarithms (1:2, 1:4, 1:8, 1:16, etc.). 10 $\mu$l of the respective dilution are added to the cultures of L929 fibroblasts on microtiter plates (5×10$^4$ cells/hole). After 48 hours of incubation at 37° C., 10% $CO_2$, and 98% humidity, the cytopathic effect is read. FIG. 1 shows the lowest dilutions which are negative.

EXAMPLE 12

Direct Antiviral Activity Against MHV3

0.5 ml of MHV3 virus suspension with a titer of 2.5×10$^3$ infectious particles/ml are incubated with various amounts of A.h. extract according to Table IV in Hepes buffered DMEM at 23° C. for one hour. 10 $\mu$l of the respective preparation are added to L929 cultures on microtiter plates and incubated for 24 hours (number of cells: 5×10$^4$/hole, incubation conditions: 37° C., 10% $CO_2$, 98% humidity). The resultant plaques are determined microscopically from eight parallel cultures.

TABLE IV

| A.h. ($\mu$g/culture) | 0 | 0.035 | 0.07 | 0.15 | 0.3 | 0.6 | 1.25 | 2.5 |
|---|---|---|---|---|---|---|---|---|
| plaques/culture | 25 | 10.5 | 3.5 | 1.3 | 0.3 | 0.2 | 0 | 0 |

EXAMPLE 13

Direct Antiretroviral Activity Against HIV

Cells of the T cell line MT4 are infected with HIV-1 (titer dilution 1:200) with or without an A.h. extract dilution (10 $\mu$l/hole) on a microtiter plate. The dilution of A.h. extract up to which HIV-1 is neutralized is determined.

We claim:

1. An extract of the *Acanthospermum hispidum* plant which contains only the water-soluble components thereof with a molecular weight >2,000.

2. A process for the production of the extract of claim 1 which comprises extracting parts of the *Acanthospermum hispidum* plant with water and then separating the ingredients with a molecular weight <2,000 from the extract.

3. The process of claim 2, wherein green leaves of the plant are used for extraction.

4. The process of claim 2, wherein dried leaves of the plant are used for extraction.

5. The process of any one of claims 2 to 4, wherein said extraction is carried out at a temperature between 4° C. and 100° C.

6. The process of claim 2, wherein said separation of the components with a molecular weight <2,000 from the extract is effected by way of dialysis.

7. The process of claim 2, wherein said separation of the components with a molecular weight <2,000 from the extract is effected by way of ammonium sulfate precipitation.

8. A method for stimulating immunomodulation which comprises administering to a patient in need of such treatment an immunomodulatory amount of the extract of the *Acanthospermum hispidum* plant of claim 1.

9. A method for stimulating an antitumor response which comprises administering to a patient in need of such treatment an antitumor amount of the extract of the *Acanthospermum hispidum* plant of claim 1.

10. A method for remedying radiation sickness which comprises administering to a patient in need of such treatment a radiation sickness remedying amount of the extract of the *Acanthospermum hispidum* plant of claim 1.

11. A method for the treatment of virus diseases in mammals which comprises administering to a patient in need of such treatment an antiviral amount of the extract of the *Acanthospermum hispidum* plant of claim 1.

12. A method for the treatment of retrovirus diseases in mammals which comprises administering to a patient in need of such treatment an antiretroviral amount of the extract of the *Acanthospermum hispidum* plant of claim 1.

13. A method for the treatment of Herpes labialis which comprises administering to a patient in need thereof an effective anti-Herpes Labialis amount of the extract according to claim 1.

* * * * *